United States Patent [19]

Kobayashi et al.

[11] 4,105,779

[45] Aug. 8, 1978

[54] ANTHELMINTIC PROCESS FOR DOMESTIC ANIMALS

[75] Inventors: Hidetoshi Kobayashi; Kohei Araki, both of Iwaki, Japan

[73] Assignee: Kureha Kagaku Kogyo Kabushiki Kaisha, Tokyo, Japan

[21] Appl. No.: 762,077

[22] Filed: Jan. 24, 1977

Related U.S. Application Data

[63] Continuation of Ser. No. 544,609, Jan. 27, 1975, abandoned, which is a continuation-in-part of Ser. No. 122,183, Mar. 8, 1971, abandoned.

[30] Foreign Application Priority Data

Mar. 10, 1970 [JP] Japan .................................. 45-19722

[51] Int. Cl.² .................. A61K 31/74; A61K 31/745; A61K 31/66
[52] U.S. Cl. ....................................... 424/78; 424/19; 424/83; 424/219
[58] Field of Search ...................... 424/19, 32, 33, 78, 424/81, 83, 219

[56] References Cited

U.S. PATENT DOCUMENTS

| 3,318,769 | 5/1967 | Folckemer et al. | 424/219 |
| 3,470,293 | 9/1969 | Riehen | 424/84 |

FOREIGN PATENT DOCUMENTS

| 42-10,399 | 5/1967 | Japan | 424/219 |
| 1,015,933 | 1/1966 | United Kingdom | 424/219 |
| 1,119,493 | 7/1968 | United Kingdom | 424/219 |
| 1,190,969 | 5/1970 | United Kingdom | 424/219 |

OTHER PUBLICATIONS

*Derwent Japanese* 28.1.1.65–3.2.65, vol. 4; #52046/63.

*Primary Examiner*—Frederick E. Waddell
*Attorney, Agent, or Firm*—Sughrue, Rothwell, Mion, Zinn and Macpeak

[57] ABSTRACT

This invention relates to a novel anthelmintic composition comprising a complex chemical compound of calcium salt of O-methyl-O-(2,2-dichlorovinyl)phosphoric acid with O, O-dimethyl-O-(2,2-dichlorovinyl)phosphate, and a specifically selected thermoplastic resin, for oral administration of the animals.

10 Claims, No Drawings

ANTHELMINTIC PROCESS FOR DOMESTIC ANIMALS

CROSS-REFERENCE TO RELATED APPLICATION

This application is a continuation application of Ser. No. 544,609, filed Jan. 27, 1975, in turn a continuation-in-part application of Ser. No. 122,183, filed Mar. 8, 1971, both of said prior applications now abandoned, by the same inventors which claim priority from Mar. 10, 1970 based upon Japanese Patent Application No. 19722/1970.

BACKGROUND OF THE INVENTION

This invention relates to a novel composition comprising a complex chemical compound of calcium O-methyl-O-(2,2-dichlorovinyl)phosphate with O,O-dimethyl-O-(2,2-dichlorovinyl)phosphate which will be referred briefly as CAVP hereinafter throughout the specification, and a specifically selected thermoplastic resin, said composition being highly effective for anthelmintic purposes through oral administration for domestic animals and poultry and representing a remarkably low mammalian toxicity.

The specifically selected thermoplastic resin in the above sense resides in a copolymer obtainable by copolymerizing 30 to 60 wt. parts of a conjugated diene compound, 70 to 40 wt. parts of at least a monomer which is selected from the group consisting of monovinyl compounds copolymerizable with the aforementioned diene compound and 0.5 – 5 wt. parts of a cross-linking agent. More specifically, the composition of the present invention is an anthelminitic for oral administration of domestic animals and poultry with low mammalian toxicity, as obtained by uniformly mixing CAVP to aforementioned copolymer or to the mixed resin compound of aforementioned copolymer with at least one of the thermoplastic resins selected from the group consisting of polymethyl methacrylate, polyvinyl chloride, polyvinyl acetate, polystyrene and a copolymer of ethylene and vinyl acetate.

The conjugated diene compound which is utilized as a monomer component in the present invention is selected from the group comprising butadiene, isoprene, chloroprene and the like.

The monovinyl monomer which is copolymerizable with aforementioned diene compound is selected from the group consisting of ethylene, propylene, styrene, vinyl chloride, vinyl acetate, acrylonitrile, methyl acrylate, vinyl butyl ether, vinylidene chloride, methacrylonitrile, α-methylstyrene and methyl methacrylate.

The active ingredient of the composition of the present invention, CAVP, is known as an organo-phosphorous insecticide having many excellent characteristics as disclosed in the Japanese Patent Publication Sho-42-10399, and the utilization of CAVP as an anthelmintic for warm-blooded animals has been applied for a Japanese patent under Patent Application Sho-43-26561.

According to the said Japanese Patent Application, the chemical compound is claimed to be low-toxic to warm-blooded animals and to have an excellent anthelmintic effectiveness.

Having continued researches for improvements in the utilization of CAVP as anthelmintic to be orally administrated to warm-blooded animals, we have now found that the composition according to the present invention is very low-toxic and superior for control of the helminths in warm-blooded animals without giving any adverse effects to such animals.

It is generally known that organo-phosphorous compounds have a high lethal effect against helminths in animal bodies. However, owing to their high mammalian toxicity, a large oral dose of them will mostly give harmful or unhealthy effects to the animals with occasional death due to their rapid adsorption in stomachs or intestines of the animals. Under occasions owing to their rapid decomposition or to their rapid adsorption in the intestines, small oral dose of the compounds may sometimes be inefficient in controlling the helminths parasiting mainly in intestines. Moreover, the warm-blooded animals are very keen in the taste and odor of the feed and medicines and they are apt to deny to take the feed when containing such animal medicines. Even when they should take the feed, it is sometimes difficult to dose effective amount of the medicine due to their liable vomiting after the administration.

SUMMARY OF THE INVENTION

The main object of the present invention is to provide an anthelmintic which is safe for the warm-blooded animals when administrated orally even in large amounts, positively effective in controlling the helminths by administrating in small amounts and very easy to administer by combining it with the feed without affecting the animal's appetite.

It is a further object of the present invention to provide an anthelmintic of the above kind, the elution of the active ingredient thereof in stomach being less than that in intestines, especially in consideration of the fact that almost all the helminths parasite in intestines.

When an anthelmintic including CAVP as its active ingredient arrives firstly at the stomach of a warm-blooded domestic animal administered with the anthelmintic, the concentration of the effective ingredient is rather high and the latter is rather more stable therein than in the intestines. At this stage, therefore, the elusive performance of the effective ingredient will be substantially higher than necessary for anthelmintic purpose thereat. It is not desirable, therefore, to have a higher concentration of the active ingredient in stomach than that which is necessary for controlling endoparasites therein because of the increase of the toxicological action of the active ingredient.

The adoption of such measure that the elusion of the effective ingredient in the intestines is higher than in the stomach serves for positive prevention of otherwise possible appearance of a higher concentration of the ingredient in the latter than in the former animal organs. In this way, the effective concentrations of the effective ingredient in the both kinds of internal animal organs will approach mostly to respective necessary anthelmintic concentrations, in addition to the realization of favorable reduction of toxicity to the animal under administration and of practically uniform anthelmintic effect throughout the whole digestive canal system of the animal.

DETAIL DESCRIPTION OF THE INVENTION

As will become more clear hereinafter as the description proceeds, the elution characteristic of the composition of the present invention is highly promising for the latter purpose. Especially, the elution characteristic of the composition will be further enhanced by compounding CAVP evenly with the aforementioned specifically selected thermoplastic resin(s) and thermally and mechanically granulating thereof.

As for prior anthelmintic composition used for oral administration to warm-blooded animals containing an organo-phosphorous active ingredient combined and processed with thermoplastic resin(s), reference may be had to Japanese Patent Publication Sho-40-2046 disclosing DDVP as an active ingredient.

However, even when utilizing various resins disclosed in said Patent Publication, it is difficult as verified by our experiments to have such a remarkable difference of elution characteristic in and between gastric juice and intestinal juice of the administered animal as is aimed at by the present invention.

According to our experiments, it was found that, when the dosage is small, the anthelmintic effectiveness is insufficient, while when the dosage is large the unhealthy and adverse effects appear on the animal bodies such as lowering of cholinesterase activity and invitation of vomiting and diarrhea phenomena.

It has been further found that the usable range of dosage of the anthelmintics proposed by the said Japanese Patent Publication Sho-40-2046, for the control of the helminths is substantially narrower than that of those of the present invention.

Especially, prior anthelmintics are liable to elute too much during passage toward and through the omasum of ruminants, and it is thus difficult to sufficiently control the helminths parasting in the abomasum and in the abomasum and intestines.

On the contrary, the anthelmintic composition of the present invention has made it possible to fully exhibit the controlling effectiveness to the helminths parasting in the abomasum and/or intestines by suitably decreasing the elution thereof during passage toward and through the omasum.

According to the test results of orally administrating as an example, 5,000 mg of the anthelmintic composition of the present invention to rats and young hogs per kg. of their body weight, the mortality of the animals was zero and a guaranteed safety of the composition was recognized.

The anthelmintic composition of the present invention has the aforementioned promising characteristics, to be administered for controlling endoparastic worms such as round worms, pinworms, whip worms, threadworms, cecal worms, stomach worms, hair worms, threadnecked worms, cooperia and the like.

For example, the composition of the present invention have been found to be effective for control of species of Haemonchus, Trichostrongylus, Ostertagia, Cooperia, Trichuris, Oesophagostomum, Strogloidea, Ascaris, Nematodirus, Gastrophilus.

The most appropriate dose rate of the composition of the present invention depends on the kind and amount of the specifically selected thermoplastic resin(s), the content of the active ingredient, the shape and kind of formulation, however, on the average, it corresponds to 10–60 mg calculated as CAVP per kg. of body weight of the animals to be administered.

On the other hand, the composition of the present invention is safe for the animal health, practically without giving any side effect even if it is administered and the dose rate corresponding to 500 mg of CAVP per kg. of the weight of animal body.

The composition of the present invention may be administered after mixing with commonly utilized insecticides, fungicides, bactericides and nutrient medicines, when necessary.

The range of content of CAVP in the composition of the present invention has practically no limitation. Optimum content thereof may be, however, 10 to 40% by weight of the composition.

In addition to the main components: CAVP and the thermoplastic resin(s), one or more various plasticizers, stabilizers, lubricating agents, colorants and inert weighting powders such as silica, clay and talc which are admixible with the thermoplastic resins may be mixed to the composition of the present invention.

When formulating the composition of the present invention it can be processed and formed to any shape and size by conventional processing methods such as molding, extrusion, casting and blowing which are utilized for the purpose. However, it will be most desirable to form the composition to granules because of the easiness of handling and administrating of the shaped composition.

Generally speaking, it is necessary to hear the thermoplastic material to the temperature of 100° C or so in order to process the plastic. However, in the case of the preparation of the composition of the present invention, unavoidable loss of the active ingredient during the heating step will be prevented easier than in the case of DDVP, because of the lower vapor pressure of the active ingredient, CAVP, in the composition of the present invention than DDVP. This is a further substantial merit of the present invention over the prior art. Moreover, the lower vapor pressure of the active ingredient according to the present invention makes it easier to suppress losses thereof during preservation and storage of the products and to provide thus favorably good preservable products.

The composition of the present invention is utilizable for controlling aquatic pest insects and effective for this purpose for a long time period.

Thus, the composition of the present invention, formulated as granules, for instance, can be suspended in a pond or sewerage where mosquito-larvae are present or in a fishpond where pest animals live on the fishes. The plates and nets formulated of the composition may be immersed in water of such aquatic area to control such pests for long time.

Several numerical examples will be given below for better understanding of the nature of the invention and in no limiting sense thereof.

EXAMPLE 1

Twenty-five parts by weight of CAVP, 60 parts by weight of a copolymer comprising 54 parts by weight of butadiene, 20 parts by weight of methyl metacrylate, 25 parts by weight of styrene and one part by weight of divinyldenzene; and 15 parts by weight of methyl methacrylate were well mixed and the mixture was extruded by an extruder as granules of 1.5 mm in mean diameter and about 3 mm in length.

EXAMPLE 2

Twenty-five parts by weight of CAVP, 70 parts by weight of a copolymer comprising 40 parts by weight of butadiene, 29.5 parts by weight of methyl methacrylate, 30 parts by weight of styrene and 0.5 parts by weight of divinyl-benzene; and 5 parts by weight of dioctyl phthalate were mixed well and the mixture was extruded by an extruder as granules of 1.5 mm in mean diameter and about 3 mm in length.

EXAMPLE 3

Twenty-five parts by weight of CAVP, 45 parts by weight of a copolymer comprising 40 parts by weight of butadiene, 29 parts by weight of methyl methacrylate, 30 parts by weight of styrene and one part by weight of divinylbenzene; and 20 parts by weight of a copolymer of ethylene and vinyl acetate and 10 parts by weight of Carplex (minute powder of silica) were well mixed. The mixture was extruded from an extruder as granules of 1.5 mm in mean diameter and about 3 mm in length.

EXAMPLE 4

Examination of Elution of the Active Ingredient in Artificial Gastric Juice and in Intestinal Juice The composition of the present invention, the details thereof being shown hereinafter, was put respectively into the artificial gastric juice and the intestinal juice designated in *Pharmacopeia Japonica*. The eluted amounts of the active ingredient were determined at 38° C, while shaking the juice at predetermined time periods. The results, in terms of percentage elution of the active ingredient at the predetermined time period, is tabulated in the following Table 1.

Table 1

| Composition | Percentage elution of the a.i. at several time period in hours. | | | | | | | |
|---|---|---|---|---|---|---|---|---|
| | artificial gastric juice | | | | artificial intestinal juice | | | |
| | 3hrs | 6hrs | 9hrs | 24hrs | 3hrs | 6hrs | 9hrs | 24hrs |
| Those in Ex. 1 | 8.4 | 13.5 | 18.7 | 25.1 | 20.3 | 33.2 | 41.9 | 58.0 |
| Those in Ex. 2 | 15.7 | 23.0 | 38.4 | 40.4 | 22.2 | 36.6 | 45.3 | 65.1 |
| Those in Ex. 3 | 12.5 | 20.2 | 24.0 | 36.1 | 28.5 | 44.1 | 56.0 | 77.5 |
| Those of other composition No. 1 (CAVP)* | 25.1 | 35.5 | 42.3 | 61.4 | 25.4 | 37.9 | 42.8 | 59.7 |
| Those of other composition No. 2 (CAVP)* | 28.7 | 45.0 | 57.2 | 85.9 | 32.4 | 47.9 | 57.0 | 88.0 |
| Composition No. 1 (DDVP)* mentioned in Jap. Pat. Publication Sho-40-2046 | 19.1 | 24.4 | 29.5 | 36.3 | 16.8 | 22.9 | 28.1 | 38.1 |
| Composition No. 2 (DDVP)* mentioned in Jap. Pat. Publication Sho-40-2046 | 19.5 | 28.0 | 34.2 | 51.7 | 21.7 | 27.6 | 35.0 | 54.1 |

*the active ingredient

As seen from Table 1, the difference of elution in and between gastric juice and intestinal juice is obtained only by use of the composition of the present invention (compositions of examples 1 to 3).

Prior compositions other than those of the present invention in Table 1 enlisted for comparison purposes are as follows:

(1) Composition No. 1 (CAVP)*:

Twenty-five parts by weight of CAVP, 65 parts by weight of polyvinyl chloride and 10 parts by weight of dioctyl phthalate were well mixed and extruded from an extruder into granules of 1.5 mm in mean diameter and about 3 mm in mean length.

(2) Composition No. 2 (CAVP)*:

Twenty-five parts by weight of CAVP and 75 parts by weight of a copolymer of ethylene and vinyl acetate were mixed well and extruded as granules of 1.5 mm in mean diameter and about 3 mm in mean length.

(3) Composition No. 1 of Japanese Patent Publication Sho-40-2046 (DDVP)*:

Twenty-parts by weight of DDVP, 70 parts by weight of polyvinyl chloride and 10 parts by weight of dioctyl phthalate were mixed well and extruded from an extruder into granules of 1.5 mm in mean diameter and about 3 mm in mean length.

(4) Composition No. 2 comprising a thermoplastic resin as used in the present invention and DDVP as the active ingredient:

Twenty parts by weight of DDVP, 60 parts by weight of a thermoplastic resin (copolymer comprising 40 parts by weight of butadiene, 30 parts by weight of methyl methacrylate, 30 parts by weight of styrene and one part by weight of divinyl-benzene; and 20 parts by weight of polymethyl methacrylate were well mixed and extruded into granules of 1.5 mm in mean diameter and about 3 mm in mean length.

EXAMPLE 5

Anthelmintic Activity of the Composition of the Present Invention When Administrated to Young Hogs 120 mg (30 mg based upon CAVP) of granules of Examples 1, 2 and 3 were respectively administrated to young hogs per kg. of hog's body weight admixtured with their feed.

The number of parasite's eggs found in their feces before and after the administration and that of parasites excreted after the administration were observed, and tabulated in the following Table 2.

According to our observation, all the feed admixture with every composition of the present invention were taken by the hogs as same as the ordinary feed containing no medicine. That is, the hogs did not shown any reluctance to the feeds containing the composition of the present invention.

Further, it was observed that every formulation of the composition of the present invention had no unhealthy effect to the young hogs.

Table 2

| | | Number of eggs and adults of the parasites found in the feces | | | |
|---|---|---|---|---|---|
| | | Composition of Ex. 1 | Composition of Ex. 2 | Composition of Ex. 3 | Control no medicine |
| Before administration Eggs | A. | 11,000 | 10,350 | 6,550 | 6,800 |
| | O. | 130 | 80 | 50 | 90 |
| | T. | 1,350 | 1,050 | 930 | 850 |
| 24hrs after administration | A. | 1,250 | 950 | 850 | 5,800 |
| | O. | 0 | 0 | 0 | 120 |

Table 2-continued

| | | Number of eggs and adults of the parasites found in the feces | | | |
|---|---|---|---|---|---|
| | | Composition of Ex. 1 | Composition of Ex. 2 | Composition of Ex. 3 | Control no medicine |
| Eggs | T. | 250 | 100 | 150 | 800 |
| 24hrs after | A. | 25 | 27 | 11 | 1 |
| administration | O. | 9 | 6 | 5 | 0 |
| Adults | T. | 58 | 62 | 58 | 3 |
| 48hrs after | A. | 400 | 200 | 400 | 6,000 |
| administration | O. | 0 | 0 | 0 | 100 |
| Eggs | T. | 20 | 0 | 20 | 1,100 |
| 48hrs after | A. | 1 | 0 | 1 | 0 |
| administration | O. | 0 | 0 | 0 | 0 |
| Adults | T. | 3 | 0 | 1 | 5 |
| 72hrs after | A. | 20 | 0 | 0 | 5,750 |
| administration | O. | 0 | 0 | 0 | 100 |
| Eggs | T. | 0 | 0 | 0 | 950 |
| 72hrs after | A. | 0 | 0 | 0 | 0 |
| administration | O. | 0 | 0 | 0 | 0 |
| Adults | T. | 0 | 0 | 0 | 5 |

N.B.
A: Ascarids
O: Oesophagostomids
T: Trichurids

As seen from Table 2, the compositions of the present invention showed excellent endoparastic-controlling effectiveness, practically completely controlling the endoparasites at the rate of 30 mg CAVP per kg. of the body weight of the young hogs.

EXAMPLE 6

Anthelmintic Experiments on Horses

Seventeen horses in total, 1–10 year old, weighing 200–600 kgs, were administrated with the composition disclosed in the foregoing Example 1 which was admixed evenly to animal feed. Two different dosages were employed, one being 200 mg/day/kg administrated for 2 successive days to 11 horses and the other being 300 mg/day/kg administrated only once to six horses.

In these experiments, presence or non-existence of large round worms (Parascaris equorum Goeze), horses strongyles (Strongylidae Baird) and/or larvae of bostflies (Gastrophilus Leach) were observed in excreta.

Finally, after 3–5 days upon the oral administration, the horses were brought to mortality for zootomical observation of remainder endoparasites. The results are tabulated in the following Table 3.

Table 3

| oral dosage | | 200 mg/kg/day administrated for two successive days | 300 mg/kg administrate once only |
|---|---|---|---|
| discharged endoparasites | large round worms | 4 horses/11 horses; (+) | 3 horses/6 horses; (+) |
| | horse strongyles | 11 horses/11 horses; (+) | 6 horses/6 horses; (+) |
| | botfly larvae | 11 horses/11 horses (+) | 11 horses/11 horses (+) |
| remainder endoparasites observed at zootomical inspection | large round worms | zero for all forces administered | same as left |
| | horse strongyles | same as above | same as left |
| | botfly larvae | same as above | 3 horses/6 horses; 6 worms in total |

From the above results, it was determined that with each of said dosages, large round worms and horse strongyles were totally driven out.

As for botfly larvae parasiting at stomach mucosae and thus highly difficult to discharge, they could be successfully discharged with dosage of 200 mg/kg for two successive days or substantially driven out with dosage of 300 mg/kg administrated once only, which means a remarkable progress in the art.

It should be noted that all the horses under administration with the composition according to this invention, admixed to animal feeds, took them with no adverse effects upon the appetite, as in the same degree with feeding the horses with regular feeds containing no such compositions. Upon administrated, no unfavorable physical and the like effects upon the animals were observed.

The embodiments of the invention in which an exclusive property or privilege is claimed are as follows:

1. A process for combatting gastro-intestinal worms in poultry or warm-blooded domestic animals which comprises orally administering to said poultry or warm-blooded domestic animals an anthelmintic effective amount of a composition comprising a complex chemical compound of the calcium salt of O-methyl-O-(2,2-dichlorovinyl)phosphoric acid with O,O-dimethyl-O-(2,2-dichlorovinyl)phosphate and a thermoplastic resin comprising a co-polymer obtained by copolymerizing 30 to 60 wt. parts of a conjugated diene compound selected from the group consisting of butadiene, isoprene and chloroprene with 70 to 40 wt. parts of a monovinyl monomer compound copolymerizable with said diene compound and selected from the group consisting of ethylene, propylene, styrene, vinyl chloride, vinyl acetate, acrylonitrile, methyl acrylate, vinyl butyl ether, vinylidene chloride, methacrylaonitrile, alpha-methylstyrene, and methacrylate, in the presence of from 0.5 to 5.0 wt. parts of divinylbenzene as a crosslinking agent.

2. The process of claim 1 wherein said diene compound is butadiene and said monovinyl monomer compound is styrene and/or methyl methacrylate.

3. A process for combatting gastro-intestinal worms in poultry or warm-blooded domestic animals which comprises orally administering to said poultry or warm-blooded domestic animals an anthelmintic effective amount of a composition comprising a complex chemical compound of the calcium salt of O-methyl-O-(2,2-dichlorovinyl)phosphoric acid with O,O-dimethyl-O-(2,2-dichlorovinyl)phosphate admixed with 100 wt. parts of a mixture comprising 40–20 wt. parts of a polymethylmethacrylate or ethylene-vinylacetate copolymer and 60–80 wt. parts of a copolymer obtained by copolymerizing 30–60 wt. parts of butadiene, 70–40 wt. parts of styrene and/or methyl methacrylate and 0.5–5.0 wt. parts of a divinylbenzene.

4. The process of claim 2 wherein said composition further comprises less than 10 wt. parts finely divided silica.

5. The process of claim 3 wherein said composition further comprises less than 10 wt. parts finely divided silica.

6. The process of claim 1 wherein said composition further comprises less than 10 wt. parts finely divided silica.

7. The process of claim 2 wherein said composition contains 10–40 wt. % of said complex chemical compound.

8. The process of claim 3 wherein said composition contains 10–40 wt. % of said complex chemical compound.

9. The process of claim 6 wherein said composition contains 10–40 wt. % of said complex chemical compound.

10. The process of claim 1 wherein said composition contains 10–40 wt. % of said complex chemical compound.

* * * * *